United States Patent
Woloszko et al.

(10) Patent No.: US 8,747,399 B2
(45) Date of Patent: Jun. 10, 2014

(54) METHOD AND SYSTEM OF REDUCTION OF LOW FREQUENCY MUSCLE STIMULATION DURING ELECTROSURGICAL PROCEDURES

(75) Inventors: Jean Woloszko, Austin, TX (US); Duane W. Marion, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 1083 days.

(21) Appl. No.: 12/754,727

(22) Filed: Apr. 6, 2010

(65) Prior Publication Data
US 2011/0245826 A1 Oct. 6, 2011

(51) Int. Cl.
A61B 18/12 (2006.01)
A61B 18/14 (2006.01)
A61B 18/00 (2006.01)

(52) U.S. Cl.
CPC ............ *A61B 18/1206* (2013.01); *A61B 18/14* (2013.01); *A61B 2018/00625* (2013.01); *A61B 2018/1213* (2013.01); *A61B 2018/1467* (2013.01)
USPC ............................................. 606/34; 606/41

(58) Field of Classification Search
CPC ........... A61B 18/1206; A61B 18/1233; A61B 18/14; A61B 2018/00625; A61B 2018/12; A61B 2018/1206; A61B 2018/1213; A61B 2018/124; A61B 2018/1467
USPC .......................................... 606/32–41, 48, 50
See application file for complete search history.

(56) References Cited

U.S. PATENT DOCUMENTS 2,050,904 A 4/1936 Trice ................................ 219/31
2,056,377 A 10/1939 Wappler ......................... 125/303
(Continued)

FOREIGN PATENT DOCUMENTS

DE 3119735 1/1983 ............. A61B 17/39
DE 3930451 A1 3/1991 ............. A61B 17/39
(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Michael Peffley
*Assistant Examiner* — Samantha Good
(74) *Attorney, Agent, or Firm* — Matthew Scheele; Brian E. Symczak

(57) ABSTRACT

Reduction of low frequency muscle stimulation during electrosurgical procedures. At least some of the illustrative embodiments are methods including: treating a target tissue with an electrosurgical wand comprising a plurality of active electrodes intermittently exposed to a rectifying electrical phenomenon; charging a first capacitance in series with a first electrode of the plurality of active electrodes, the charging during periods of time when the rectifying electrical phenomenon proximate the first electrode; charging a second capacitance in series with a second electrode of the plurality of active electrodes, the charging during periods of time when the rectifying electrical phenomenon is proximate the second electrode; charging a third capacitance in series with a third electrode of the plurality of active electrodes, the charging during periods of time when the rectifying electrical phenomenon is proximate the third electrode; and discharging, through the first electrode, the first capacitance, while simultaneously charging the second capacitance.

8 Claims, 7 Drawing Sheets

(56) References Cited

U.S. PATENT DOCUMENTS

| | | | |
|---|---|---|---|
| 2,611,365 A | 9/1952 | Rubens | 606/42 |
| 3,434,476 A | 3/1969 | Shaw et al. | 606/22 |
| 3,633,425 A | 1/1972 | Sanford | 73/356 |
| 3,707,149 A | 12/1972 | Hao et al. | 128/303.14 |
| 3,718,617 A | 2/1973 | Royal | 260/30.4 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,963,030 A | 6/1976 | Newton | 606/40 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| D249,549 S | 9/1978 | Pike | D24/144 |
| 4,114,623 A | 9/1978 | Meinke et al. | 606/39 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,301,801 A | 11/1981 | Schneiderman | 606/38 |
| 4,326,529 A | 4/1982 | Doss et al. | 128/303 |
| 4,346,715 A | 8/1982 | Gammell | 607/99 |
| 4,363,324 A | 12/1982 | Kusserow | 607/64 |
| 4,378,801 A | 4/1983 | Oosten | 606/37 |
| 4,381,007 A | 4/1983 | Doss | 128/303 |
| 4,418,692 A | 12/1983 | Guay | 606/42 |
| 4,474,179 A | 10/1984 | Koch | 606/40 |
| 4,476,862 A | 10/1984 | Pao | 128/303 |
| 4,509,532 A | 4/1985 | DeVries | 128/736 |
| 4,520,818 A | 6/1985 | Mickiewicz | 606/40 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,750,902 A | 6/1988 | Wuchinich et al. | 604/22 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,846,179 A | 7/1989 | O'Conner | 607/72 |
| 4,860,752 A | 8/1989 | Turner | 607/102 |
| 4,898,169 A | 2/1990 | Norman et al. | 606/42 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,026,387 A | 6/1991 | Thomas | 606/169 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins et al. | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,174,304 A | 12/1992 | Latina et al. | 607/141 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,342,357 A | 8/1994 | Nardella | 606/40 |
| 5,348,554 A | 9/1994 | Imran et al. | 606/41 |
| 5,363,324 A | 11/1994 | Hashimoto et al. | 365/156 |
| 5,366,443 A | 11/1994 | Eggers et al. | 252/511 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,874 A | 1/1995 | Jackson et al. | 606/1 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |

(56) References Cited

U.S. PATENT DOCUMENTS

| | | | |
|---|---|---|---|
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards | 606/41 |
| 5,507,743 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,700,262 A | 12/1997 | Acosta et al. | 606/48 |
| 5,715,817 A | 2/1998 | Steven-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A | 12/2000 | Meyer-ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |

(56) References Cited

U.S. PATENT DOCUMENTS

| | | | |
|---|---|---|---|
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,425,912 B1 | 7/2002 | Knowlton | 607/101 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,500,173 B2 | 12/2002 | Underwood et al. | 606/32 |
| 6,514,248 B1 | 2/2003 | Eggers et al. | 606/41 |
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,640,128 B2 | 10/2003 | Vilsmeier et al. | 600/427 |
| 6,656,177 B2 | 12/2003 | Truckai et al. | 606/51 |
| 6,663,554 B2 | 12/2003 | Babaev | 600/2 |
| 6,663,627 B2 | 12/2003 | Francischelli et al. | 606/41 |
| 6,702,810 B2 | 3/2004 | McClurken et al. | 606/34 |
| 6,730,080 B2 | 5/2004 | Harano et al. | 606/38 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| D493,530 S | 7/2004 | Reschke | D24/144 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,780,184 B2 | 8/2004 | Tanrisever | 606/45 |
| 6,802,842 B2 | 10/2004 | Ellman et al. | 606/45 |
| 6,830,558 B2 | 12/2004 | Flaherty et al. | 604/67 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,864,686 B2 | 3/2005 | Novak et al. | 324/419 |
| 6,866,671 B2 | 3/2005 | Tierney et al. | 606/130 |
| 6,872,183 B2 | 3/2005 | Sampson et al. | 600/561 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,921,398 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,953,461 B2 | 10/2005 | McClurken et al. | 606/51 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 606/41 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,223,265 B2 | 5/2007 | Keppel | 606/41 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,271,363 B2 | 9/2007 | Lee et al. | 219/121.43 |
| 7,276,061 B2 | 10/2007 | Schaer et al. | 607/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,527,624 B2 | 5/2009 | Dubnack et al. | 606/41 |
| 7,572,251 B1 | 8/2009 | Davison et al. | 604/500 |
| 7,632,267 B2 | 12/2009 | Dahla | 606/41 |
| 7,678,069 B1 | 3/2010 | Baker et al. | 604/22 |
| 7,691,101 B2 | 4/2010 | Davison et al. | 606/41 |
| 7,699,830 B2 | 4/2010 | Martin | 604/540 |
| 7,722,601 B2 | 5/2010 | Wham et al. | 606/34 |
| 7,785,322 B2 | 8/2010 | Penny et al. | 606/34 |
| 7,824,398 B2 | 11/2010 | Woloszko et al. | 606/32 |
| 7,862,560 B2 | 1/2011 | Marion | 606/34 |
| 7,985,072 B2 | 7/2011 | Belikov et al. | 433/215 |
| D658,760 S | 5/2012 | Cox et al. | D24/144 |
| 8,192,424 B2 | 6/2012 | Woloszko | 606/40 |
| 8,257,350 B2 | 9/2012 | Marion | 606/38 |
| 8,372,067 B2 | 2/2013 | Woloszko et al. | 606/34 |
| 2002/0029036 A1 | 3/2002 | Goble et al. | 606/38 |
| 2002/0042612 A1 | 4/2002 | Hood et al. | 606/50 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2003/0232048 A1 | 12/2003 | Yang et al. | 424/141.1 |
| 2004/0030330 A1 | 2/2004 | Brassell et al. | 606/41 |
| 2004/0116922 A1 | 6/2004 | Hovda et al. | 606/41 |
| 2004/0127893 A1 | 7/2004 | Hovda | 606/41 |
| 2004/0186418 A1 | 9/2004 | Karashima | 604/20 |
| 2004/0230190 A1 | 11/2004 | Dahla et al. | 606/41 |
| 2005/0004634 A1 | 1/2005 | Hovda et al. | 606/41 |
| 2005/0033278 A1 | 2/2005 | McClurken et al. | 606/34 |
| 2005/0119650 A1 | 6/2005 | Sanders et al. | 424/426 |
| 2005/0245923 A1 | 11/2005 | Christopherson et al. | 606/41 |
| 2005/0251134 A1 | 11/2005 | Woloszko et al. | 606/32 |
| 2005/0261754 A1 | 11/2005 | Woloszko et al. | 606/32 |
| 2005/0273091 A1 | 12/2005 | Booth et al. | 607/99 |

(56) References Cited

U.S. PATENT DOCUMENTS

| | | | |
|---|---|---|---|
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0161148 A1 | 7/2006 | Behnke | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0004621 A1 | 1/2008 | Dahla et al. | 606/48 |
| 2008/0077128 A1 | 3/2008 | Woloszko et al. | 606/41 |
| 2008/0138761 A1 | 6/2008 | Pond | 433/29 |
| 2008/0140069 A1 | 6/2008 | Filloux et al. | 606/41 |
| 2008/0154255 A1 | 6/2008 | Panos et al. | 606/33 |
| 2008/0167645 A1 | 7/2008 | Woloszko | 606/40 |
| 2008/0234671 A1 | 9/2008 | Marion | 606/41 |
| 2008/0243116 A1 | 10/2008 | Anderson | 606/41 |
| 2008/0300590 A1 | 12/2008 | Horne et al. | 606/35 |
| 2009/0209956 A1 | 8/2009 | Marion | 606/34 |
| 2009/0222001 A1 | 9/2009 | Greeley | 606/33 |
| 2009/0318915 A1* | 12/2009 | Hosier et al. | 606/33 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2012/0083782 A1 | 4/2012 | Stalder et al. | 606/41 |
| 2012/0095453 A1 | 4/2012 | Cox et al. | 606/33 |
| 2012/0095454 A1 | 4/2012 | Cox et al. | 606/33 |
| 2012/0109123 A1 | 5/2012 | Woloszko et al. | 606/45 |
| 2012/0196251 A1 | 8/2012 | Taft et al. | 433/216 |
| 2012/0197344 A1 | 8/2012 | Taft et al. | 607/51 |
| 2012/0215221 A1 | 8/2012 | Woloszko | 606/50 |
| 2012/0296328 A1 | 11/2012 | Marion | 606/34 |

FOREIGN PATENT DOCUMENTS

| | | | |
|---|---|---|---|
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 98/56324 | 12/1998 | A61F 7/12 |
| WO | 99/20213 | 4/1999 | A61F 7/12 |
| WO | 99/51155 | 10/1999 | A61B 17/36 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | A61F 7/12 |
| WO | 00/62685 | 10/2000 | A61B 17/20 |
| WO | 01/24720 | 4/2001 | A61B 18/18 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/102255 | 12/2002 | A61B 17/20 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2007/006000 | 1/2007 | A61B 18/14 |
| WO | 2007/056729 | 5/2007 | A61B 18/14 |
| WO | 2010/052717 | 5/2010 | A61B 18/14 |
| WO | 2012/050636 | 4/2012 | A61B 18/14 |
| WO | 2012/050637 | 4/2012 | A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.

(56) References Cited

OTHER PUBLICATIONS

Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Electrocautery on Fresh Human Articular Cartilage", J. Arthro. Surg., vol. 1, pp. 242-246, 1985.
Slager et al., "Electrical nerve and Muscle Stimulation by Radio Frequency Surgery: Role of Direct Current Loops Around the Active Electrode", IEEE Transactions on Biomedical engineering, vol. 40, No. 2, pp. 182-187, Feb. 1993.
European Examination Report for EP 02773432 4 pgs, Sep. 22, 2009.
European Examination Report for EP 05024974 4 pgs, Dec. 5, 2008.

(56) References Cited

OTHER PUBLICATIONS

European Examination Report for EP 04708664 7pgs, Sep. 7, 2009.
European Examination Report for EP 02749601.7 4pgs, Dec. 2, 2009.
European Search Report for EP 02773432 3pgs, Dec. 19, 2008.
European Search Report for EP 04708664.0 5pgs, Apr. 6, 2009.
European Search Report for EP 98953859, 2 pgs, Jul. 2, 2001.
Suppl European Search Report for EP 98953859, 3 pgs, Oct. 18, 2001
Extended European Search Report for EP09152846, 8pgs, Jan. 5, 2010.
European Search Report for EP 99945039.8, 3 pgs, Oct. 1, 2001.
PCT International Preliminary Examination Report for PCT/US02/19261, 3 pgs, Mar. 25, 2003.
PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Jul. 7, 2000.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
European Examination Report (2nd) for EP 04708664 5pgs, May 3, 2010.
European Examination Report (3rd) for EP 04708664 6pgs, Nov. 6, 2012.
European Search Report for EP 09152850, 2 pgs, Dec. 29, 2009.
PCT Notification of the International Search Report and Written Opinion for PCT/US2011/033784 11 pgs, Mailed Jul. 18, 2011.
PCT Notification of the International Search Report and Written Opinion for PCT/US2011/033761 11 pgs, Mailed Jul. 22, 2011.
UK Search Report for GB1110342.1 3pgs, Oct. 18, 2011.
UK Suppl Search Report for GB1110342.1 2pgs, Aug. 16, 2012.

\* cited by examiner

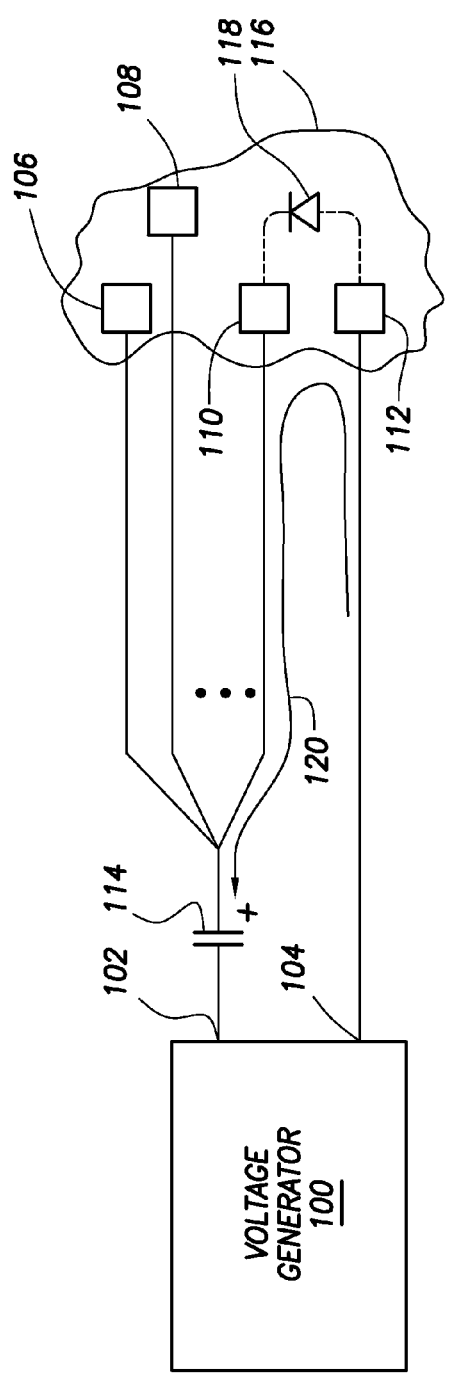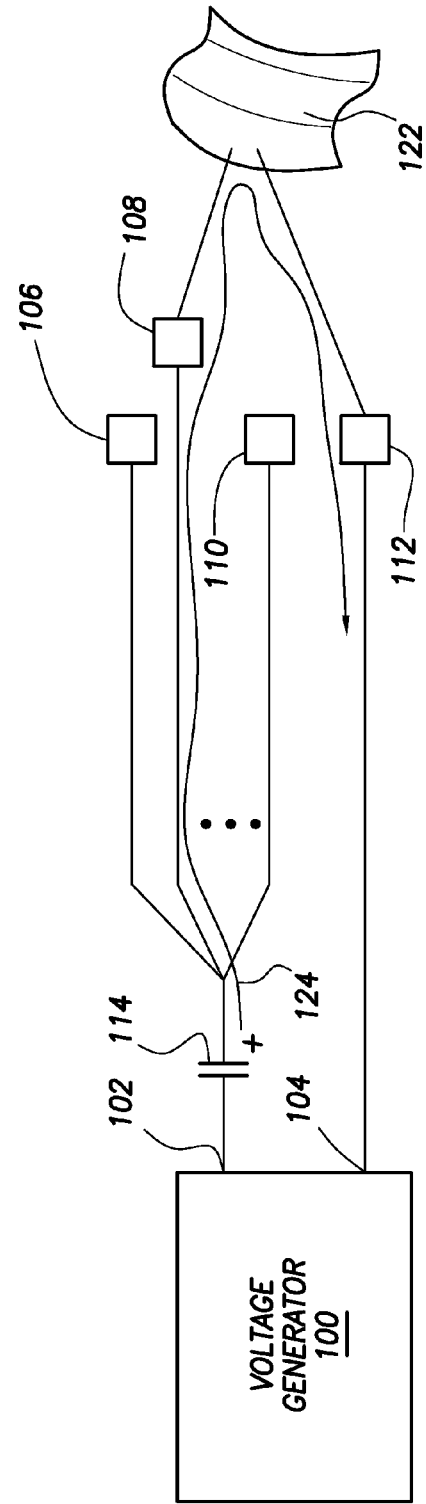

METHOD AND SYSTEM OF REDUCTION OF LOW FREQUENCY MUSCLE STIMULATION DURING ELECTROSURGICAL PROCEDURES

BACKGROUND

Electrosurgical systems are used by physicians to perform specific functions during surgical procedures. For example, in an ablation mode electrosurgical systems use high frequency electrical energy to remove soft tissue such as sinus tissue, adipose tissue or meniscus, cartilage and/or sinovial tissue in a joint. In a coagulation mode, the electrosurgical device may aid the surgeon in reducing internal bleeding by assisting in the coagulation and/or sealing of vessels.

The electrosurgical procedures are performed using high frequency signals, as such high frequency signals provide the desired electrosurgical effect and in theory should not result in muscle or nerve stimulation of the patient. Stated another way, unwanted muscle and nerve stimulation is induced by low frequency and/or direct current (DC) signals flowing across or through muscle or nerve. Equipment constructed in accordance with the International Electrotechnical Commission (IEC) standards use DC blocking capacitance between the voltage generator of the electrosurgical controller and the patient to block DC signals flowing to or from the voltage generator.

However, in spite of being constructed in accordance with IEC standards, muscle and/or nerve stimulation is still noted in some patients.

BRIEF DESCRIPTION OF THE DRAWINGS

For a detailed description of exemplary embodiments, reference will now be made to the accompanying drawings in which:

FIG. 1A shows charging of a lumped blocking capacitance in an electrosurgical procedure;

FIG. 1B shows a discharging of a lumped blocking capacitance in an electrosurgical procedure;

NOTATION AND NOMENCLATURE

Figure 2:
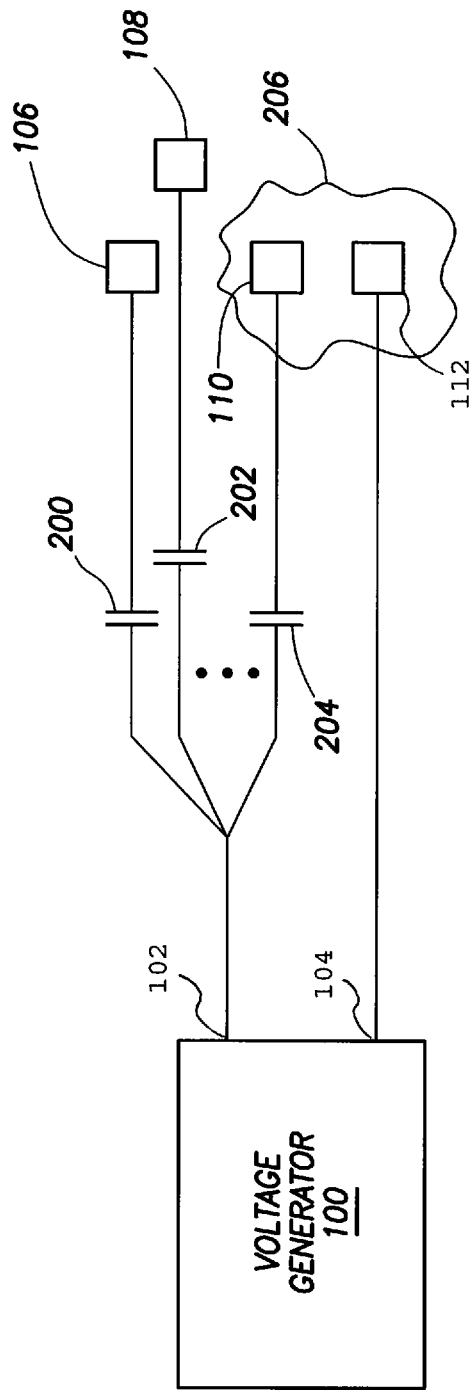
FIG. 2 shows discrete capacitances in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Return electrode" shall mean an electrode of an electrosurgical wand which serves to provide a current flow path for electrons with respect to an active electrode, and/or an electrode of an electrical surgical wand which does not itself produce an electrically-induced tissue-altering effect on tissue targeted for treatment.

"Rectifying electrical phenomenon" shall mean arcing, ionization or plasma creation proximate to an active electrode where the arcing, ionization or plasma has at least a slight electrical rectifying property.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The inventors of the present specification have uncovered a reason for parasitic stimulation of muscle and nerves of a patient by DC and/or low frequency signals in spite of electrosurgical systems using high frequency signals and a lumped blocking capacitance in accordance with IEC Standards. FIG. 1A illustrates a simplified system in order to explain the presence of parasitic DC and low frequency signals. In particular, FIG. 1A illustrates a voltage generator 100 having an active terminal 102 and a return terminal 104. The voltage generator is coupled to a plurality of active electrodes 106, 108 and 110, and as illustrated a single return electrode 112. In accordance with IEC standards the illustrative system of FIG. 1A has a direct current (DC) blocking capacitance in the form of a single DC blocking capacitor 114 coupled between the active terminal 102 and the various active electrodes.

In operation, each active electrode 106, 108 and 110 creates an electrical phenomenon 116 proximate to the active electrodes. The electrical phenomenon is in most cases an electrical arcing, ionization and/or plasma. Regardless of the precise nature of the electrical phenomenon, the electrical phenomenon has an inherent electrical rectifying characteristic, and thus is termed herein a "rectifying electrical phenomenon." The rectifying nature of the electrical phenomenon is illustrated by the diode 118 shown within the electrical phenomenon 116; however, it is to be understood that the rectifying electrical phenomenon produces a rectifying effect associated with each active electrode when the rectifying electrical phenomenon is proximate to each active electrode. Moreover, the rectifying electrical phenomenon is neither itself a diode, nor is the rectifying electrical phenomenon as efficient at rectification as a diode coupled between the electrodes. Rather, the rectifying effect is slight, and although shown to favor electrical current flow from the return electrode 112 to the active electrode 110, in some situations rectifying electrical phenomenon favors current flow from the active electrode(s) to the return electrode(s) 112. The rectifying electrical phenomenon results in a charging of the DC blocking capacitor 114. In particular, the rectifying electrical phenomenon, when present, builds a DC bias on the capacitor 114, as illustrated by the line 120 and "plus" symbol on the capacitor 114 plate. The charge continues to accumulate through each active electrode 106, 108 and 110 during periods of time when the rectifying electrical phenomenon is proximate each active electrode, and thus may build for extended periods (relative to the period of the AC signal generated by the voltage generator).

However, the rectifying electrical phenomenon is not continuous during electrosurgical procedures. That is, the rectifying electrical phenomenon is present for a time, and then may cease for a time, depending on factors such as proximity of the active electrodes to bodily tissue, and the amount and location of conductive fluid relative to the active electrode, just to name a few. The inventors have found that during periods of time when the rectifying electrical phenomenon is absent, if an active electrode physically contacts the patient, an electrical circuit is created which discharges the charge stored on the blocking capacitor 114 through the patient. FIG. 1B illustrates such a situation. In particular, FIG. 1B illustrates the situation where the rectifying electrical phenomenon has ceased proximate to active electrodes 106, 108 and 110, and further that active electrode 108 contacts the patient 122. Having active electrode 108 complete the electrical circuit is merely illustrative, as any one active electrode singly, or two more active electrodes together, may complete the electrical circuit by contacting the tissue and/or fluid of the patient. In contacting the patient 122, a completed electrical circuit is created such that the charge stored on the DC blocking capacitor 114 is discharged through the patient, as shown by line 124. The charge stored on the DC blocking capacitor 114 is a DC charge, and thus discharging the DC blocking capacitor can be considered a DC current flow. Moreover, if the electrical circuit through the patient is created periodically (e.g., 100 times a second or less), then the discharging of the DC blocking capacitor appears as a low frequency (e.g., 100 Hertz) parasitic stimulation.

Thus, having the DC blocking capacitance lumped as shown in FIGS. 1A and 1B results in large energy storage capability for the DC blocking capacitance, and further results in each and every active electrode that is involved in completing and electrical circuit discharging the energy through the patient.

In order to at least partially address these issues, electrosurgical systems in accordance with the various embodiments distribute the DC blocking capacitance across active electrodes. FIG. 2 illustrates such a system. In particular, rather than lumping the DC blocking capacitance, the system comprises a plurality of capacitors 200, 202 and 204, and wherein the plurality of capacitors are electrically coupled one each in series with a respective electrical lead and active electrode 106, 108, and 110 as illustrated by FIG. 2. While FIG. 2 shows only three electrical leads coupled to active electrodes, two or more active electrodes are contemplated, and in some cases 23 active electrodes each having a 2.2 nano-Farad (nF) capacitor in series therewith. While at first blush the circuit of FIG. 2 may seem electrically equivalent to the lumped DC blocking capacitance 114 of FIGS. 1A and 1B, a surprising result is obtained in embodiments constructed as in FIG. 2.

In particular, the inventors of the present specification have found that the rectifying electrical phenomenon is discontinuous during electrosurgical procedures with respect to each active electrode considered individually. That is, for a particular active electrode the rectifying electrical phenomenon randomly is present for a time, then ceases for a time, and then again present. During periods of time when the rectifying electrical phenomenon has ceased for the particular active electrode, other active electrodes may continue to have their respective rectifying electrical phenomenon present. For example, active electrode 110 may have its respective rectifying electrical phenomenon 206 present, but active electrodes 106 and 108 may not. Thus, in the illustrative situation capacitor 204 may be being charged with a DC bias voltage, while capacitors 200 and 202 retain their charge and/or discharge through the patient. The randomization of the discharge states of the capacitors 200, 202 and 204 surprisingly results in an effective capacitance seen by the patient during electrosurgical procedures lower than the sum of the capacitances in parallel, and thus lower than the electrosurgical systems in FIGS. 1A and 1B.

Although the inventors do not wish to be tied to any particular physical interpretation that results in the lower effective capacitance, it is believed that a portion of the lower effective capacitance is based on the lower amount of energy that can be discharged through each active electrode. While in the systems of FIGS. 1A and 1B any active electrode could discharge the full energy storage of the DC blocking capacitor 114, in the embodiments of FIG. 2 each electrode can only discharges its respective capacitor (e.g., the energy stored on capacitor 200 can only be discharged through active electrode 106). Moreover, with lower energy stored on each capacitor, a capacitor may discharge more quickly, rather than partial discharges that may occur for a lumped DC blocking capacitance. Relatedly, another physical aspect that may result in the lower effective capacitance is limited charging pathways for each capacitor 200, 202 and 204. In particular, the DC current flowing through an active electrode caused by the rectifying electrical phenomenon can only charge the respective capacitor of the active electrode. Thus, the amount of charge accumulated on a capacitor during periods of time when the rectifying electrical phenomenon associated with a particular active electrode may be lower than if electrical current through any or all active electrodes can contribute to the stored charge.

The embodiments of FIG. 2 do not intimate any particular physical location of the capacitors coupled one each in series with a respective electrical lead (or respective active electrode), and the physical placement may vary from embodiment-to-embodiment. The specification now turns to various embodiments of the electrosurgical controllers and wands, and various illustrative locations for physical placement of the respective capacitors.

Figure 3:
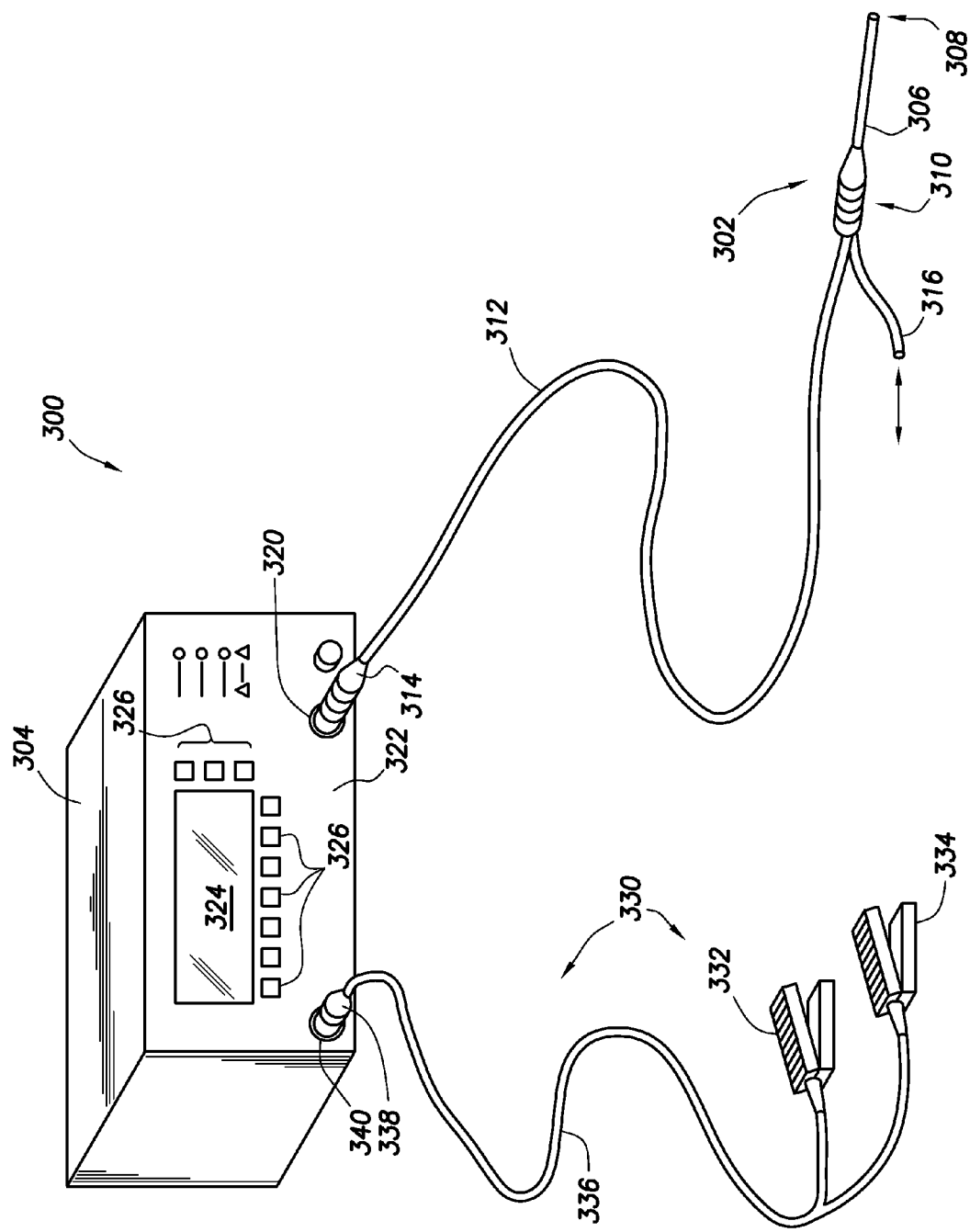
FIG. 3 shows an electrosurgical system in accordance with at least some embodiments.

FIG. 3 illustrates an electrosurgical system 300 in accordance with at least some embodiments. In particular, the electrosurgical system comprises an electrosurgical wand 302 (hereinafter "wand") coupled to an electrosurgical controller 304 (hereinafter "controller"). The wand 302 comprises an elongate shaft 306 that defines distal end 308 where at least some electrodes are disposed. The elongate shaft 306 further defines a handle or proximal end 310, where a physician grips the wand 302 during surgical procedures. The wand 302 further comprises a flexible multi-conductor cable 312 housing a plurality of electrical leads (not specifically shown in FIG. 3), and the flexible multi-conductor cable 312 terminates in a wand connector 314. Though not visible in the FIG. 3, in some embodiments the wand 302 has an internal passage fluidly coupled to a flexible tubular member 316. The internal passage and flexible tubular member 316 may be used as a conduit to supply conductive fluid proximate to the distal end 308, or the internal passage and flexible tubular member may be used to aspirate the area proximate to the distal end 308 of the wand 302.

As shown in FIG. 3, the wand 302 couples to the controller 304, such as by a controller connector 320, on an outer surface of an enclosure 322 (in the illustrative case of FIG. 3 the controller connector 320 is on a front surface). A display device or interface panel 324 is visible through the enclosure 322, and in some embodiments a user may select operational modes of the controller 304 by way of the interface device 324 and related buttons 326.

Still referring to FIG. 3, in some embodiments the electrosurgical system 300 also comprises a foot pedal assembly 330. The foot pedal assembly 330 may comprise one or more pedal devices 332 and 334, a flexible multi-conductor cable 336 and a pedal connector 338. While only two pedal devices 332, 334 are shown, any number of pedal devices may be implemented. The enclosure 322 of the controller 304 may comprise a corresponding connector 340 that couples to the pedal connector 338. A physician may use the foot pedal assembly 330 to control various aspects of the controller 304, such as the operational mode. For example, a pedal device, such as pedal device 332, may be used for on-off control of the application of radio frequency (RF) energy to the wand 302, and more specifically for control of energy in an ablation mode. A second pedal device, such as pedal device 334, may be used to control and/or set the operational mode of the electrosurgical system. For example, actuation of pedal device 334 may switch between ablation mode and a coagulation mode. Alternatively, pedal device 334 may be used to control the application of RF energy to wand 302 in a coagulation mode. The pedal devices may also be used to change the voltage level delivered to wand 302.

The electrosurgical system 300 of the various embodiments may have a variety of operational modes. One such mode employs Coblation® technology. In particular, the assignee of the present disclosure is the owner of Coblation® technology. Coblation® technology involves the application of a RF signal between one or more active electrodes and one or more return electrodes of the wand 302 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments the electrically conductive fluid is delivered in the vicinity of the active electrodes and/or to the target site by the wand 302, such as by way of the internal passage and flexible tubular member 316.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 300 of FIG. 3 is also useful for sealing larger arterial vessels (e.g., on the order of about 1 mm in diameter), when used in what is known as a coagulation mode. Thus, the system of FIG. 3 may have an ablation mode where RF energy at a first voltage is applied to one or more active electrodes sufficient to effect molecular dissociation or disintegration of the tissue, and the system of FIG. 3 has a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 300 at the distal end 308 of the wand 302 may be varied by adjusting a variety of factors, such as: the number of active electrodes; electrode size and spacing; electrode surface area; asperities and/or sharp edges on the electrode surfaces; electrode materials; applied voltage; electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 300 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Figure 4:
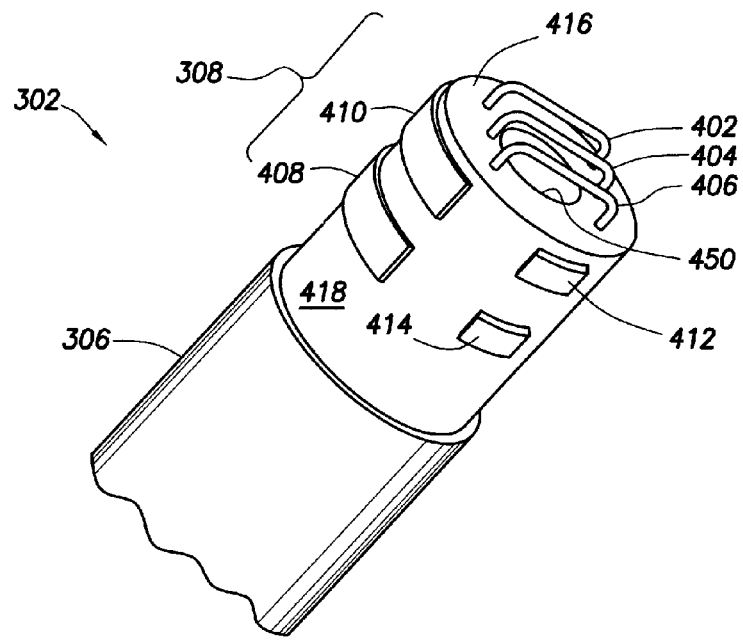
FIG. 4 shows a perspective view a portion of a wand in accordance with at least some embodiments.

FIG. 4 illustrates the distal end 308 of illustrative wand 302. In particular, in some embodiments the elongate shaft 306 is made of an inorganic insulating (i.e., non-conductive) material. In other embodiments, the elongate shaft 306 comprises a conductive material, but is covered with an insulating material. The distal end 308 further comprises a plurality of electrodes. For example, in the illustrative case of FIG. 4, seven electrodes 402, 404, 406, 408, 410, 412 and 414 are shown; however, three or more electrodes may be equivalently used. As illustrated in FIG. 4, the electrodes may take many forms. Electrodes 402, 404 and 406 are illustrative of wire-type electrodes that protrude slightly from the end 416 of the elongate shaft 306. The wire-type electrodes 402, 404 and 406 may be used, for example, singly or in combination to be the electrodes to which the RF energy is applied in the ablation mode. Electrodes 408, 410 are disposed on a surface 418 of the distal end 308, and the electrodes 408, 410 span a certain circumferential distance. Electrodes 412, 414 are similar to electrodes 408, 410, but span a smaller circumferential distance. Other electrode types, such as button electrodes (i.e., round electrodes), arrays of button electrodes, or screen electrodes, may be equivalently used.

Still referring to FIG. 4, in some embodiments the wand 302 has an internal lumen 450 that fluidly couples to the flexible tubular member 316 (FIG. 1). In some modes of operation, the internal lumen 450 is used to supply conductive fluid to the target area to aid in implementing the Coblation® technology. In other modes of operation, the internal lumen 450 may be used to aspirate the area near the distal end 308 of the wand 302, such as when sufficient conductive fluid is already present at the target location and ablation is taking place, or to remove byproducts of the ablation process.

Figure 5:
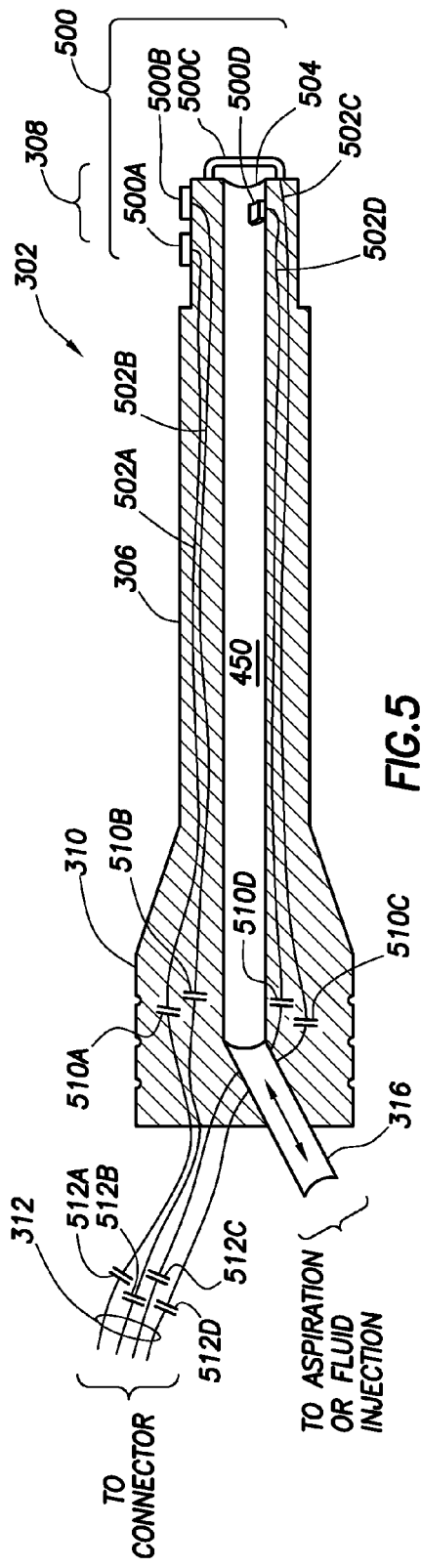
FIG. 5 shows a cross-sectional view of a wand in accordance with at least some embodiments.

FIG. 5 shows a cross-sectional view of wand 302 in accordance with at least some embodiments. In particular, FIG. 5 illustrates the elongate shaft 306 comprising distal end 308 and proximal end 310. Distal end 308 comprises a plurality of electrodes 500, and while the electrodes 500 are similar to the electrodes of FIG. 4, electrodes 500 are not necessarily the same as those of FIG. 4. Each electrode 500 has an electrical lead associated therewith that runs through the elongate shaft 306 to the flexible multi-conductor cable 312. In particular, electrode 500A has dedicated electrical lead 502A which runs within the elongate shaft to the become part of cable 312. Similarly, electrode 500B has dedicated electrical lead 502B which runs within the elongate shaft 306 to become part of cable 312. Illustrative electrodes 500C and 500D likewise have dedicated electrical leads 502C and 502D which run within the elongate shaft 306 to become part of cable 312. In some embodiments, the elongate shaft 306 has dedicated internal passages (in addition to internal lumen 450) through which the electrical leads 502 run. In other embodiments, the electrical leads 502 are cast within the material that makes up the elongate shaft.

FIG. 5 also illustrates internal lumen 450 having an aperture 504 fluidly coupled to the flexible tubular member 316 on the proximal end 310. In other embodiments, the fluid coupling of the internal lumen 450 to the flexible tubular member 316 may be between the distal end 308 and proximal end 310. The internal lumen 450 is used in some embodiments to supply conductive fluid through the aperture 504 to the target area, and in other embodiments the internal lumen 450 is used for aspiration of ablated tissue fragments and/or molecules. In some embodiments, an electrode 502D may be disposed within the internal lumen 450 proximate to the aperture 504. An electrode 500D within the internal lumen 450 may, for example, be selected as either an active or return electrode in an ablation mode, and may aid in disassociation of tissue pieces into smaller pieces during ablation and aspiration procedures.

In accordance with at least some embodiments, the plurality of capacitors coupled one each in series with a respective electrical lead may be disposed within the wand 302 as shown in FIG. 5. In particular, for the illustrative four active electrodes 500A-500D, there may be a respective four capacitors 510A-510D disposed within wand 302 (and as illustrated in the handle 310). In other embodiments the capacitors may be disposed within the elongate shaft 306.

FIG. 5 also illustrates embodiments where the plurality of capacitors coupled one each in series with a respective electrical lead may be disposed within the multi-conductor cable 312. In particular, for the illustrative four active electrodes 500A-500D, there may be a respective four capacitors 512A-

512D disposed within multi-conductor cable 312. While FIG. 5 shows capacitors both in the multi-conductor cable 312 and in the wand 302, and an electrosurgical system would be operational as illustrated in FIG. 5, when disposing the plurality of capacitors outside the controller 304 either location alone will suffice.

In addition to the distributed capacitors, current-limiting resistors may be selected. The current-limiting resistors will have a large positive temperature coefficient of resistance so that, as the current level begins to rise for any individual active electrode in contact with a low resistance medium (e.g., saline or blood), the resistance of the current limiting resistor increases significantly, thereby reducing the power delivery from the active electrode into the low resistance medium. In some embodiments, the current limited devices may reside within the elongate shaft 306, or may reside within the cable 312.

Figure 6:
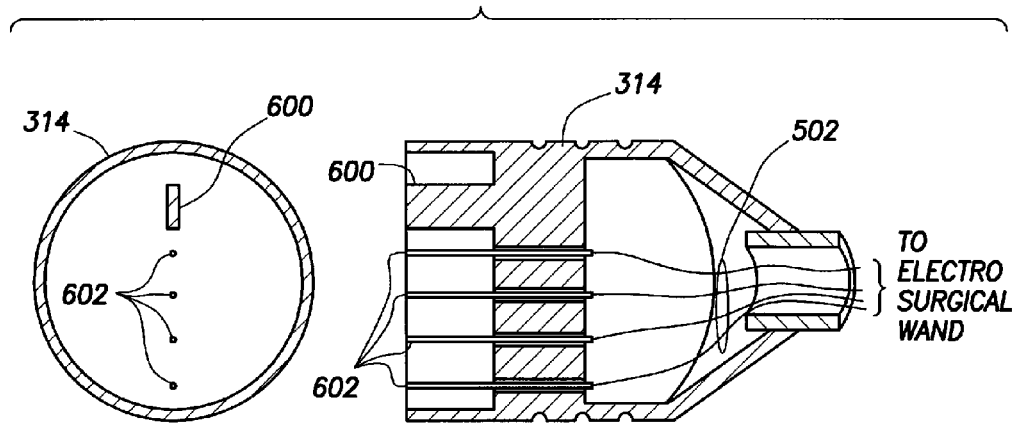
FIG. 6 shows both an elevation end-view (left) and a cross-sectional view (right) of a wand connector in accordance with at least some embodiments.

As illustrated in FIG. 3, flexible multi-conductor cable 312 (and more particularly its constituent electrical leads 502) couple to the wand connector 314. Wand connector 314 couples the controller 304, and more particularly the controller connector 320. FIG. 6 shows both a cross-sectional view (right) and an end elevation view (left) of wand connector 314 in accordance with at least some embodiments. In particular, wand connector 314 comprises a tab 600. Tab 600 works in conjunction with a slot on controller connector 320 (shown in FIG. 6) to ensure that the wand connector 314 and controller connector 320 only couple in one relative orientation. The illustrative wand connector 314 further comprises a plurality of electrical pins 602 protruding from wand connector 114. The electrical pins 402 are coupled one each to a single electrical lead 502. Stated otherwise, each electrical pin 602 couples to a single electrical lead 502, and thus each illustrative electrical pin 602 couples to a single electrode 500 (FIG. 5). While FIG. 6 shows only four illustrative electrical pins, in some embodiments 26 or more electrical pins may be present in the wand connector 314.

Figure 7:
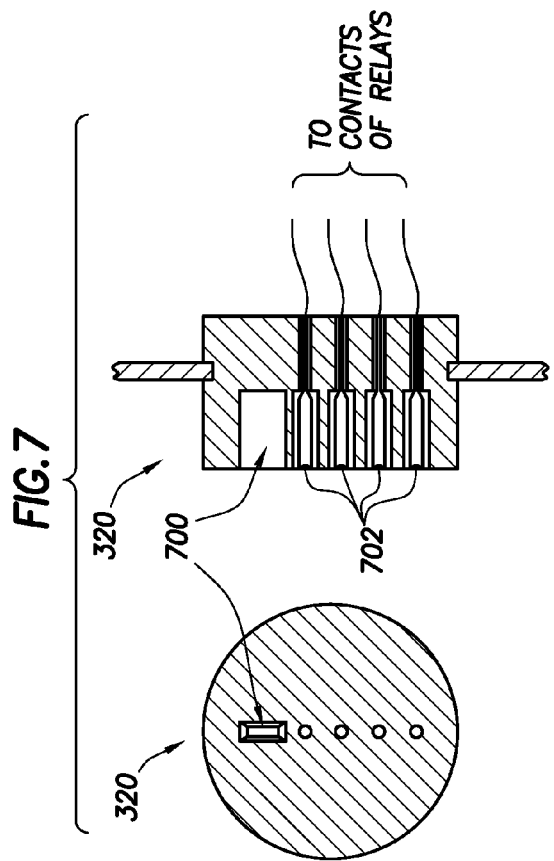
FIG. 7 shows both an elevation end-view (left) and a cross-sectional view (right) of a controller connector in accordance with at least some embodiments.

FIG. 7 shows both a cross-sectional view (right) and an end elevation view (left) of controller connector 320 in accordance with at least some embodiments. In particular, controller connector 320 comprises a slot 700. Slot 700 works in conjunction with a tab 600 on wand connector 314 (shown in FIG. 6) to ensure that the wand connector 314 and controller connector 320 only couple in one orientation. The illustrative controller connector 320 further comprises a plurality of electrical pins 702 residing with respective holes of controller connector 320. The electrical pins 702 may be individually coupled to a relay within the controller 304 (discussed more thoroughly below). When wand connector 314 and controller connector 320 are coupled, each electrical pin 702 couples to a single electrical pin 602, and thus each illustrative electrical pin 702 couples to a single electrode 500 (FIG. 5). While FIG. 7 shows only four illustrative electrical pins, in some embodiments 26 or more electrical pins may be present in the wand connector 120.

While illustrative wand connector 314 is shown to have the tab 600 and male electrical pins 602, and controller connector 320 is shown to have the slot 700 and female electrical pins 702, in alternative embodiments the wand connector has the female electrical pins and slot, and the controller connector 120 has the tab and male electrical pins. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used.

Figure 8:
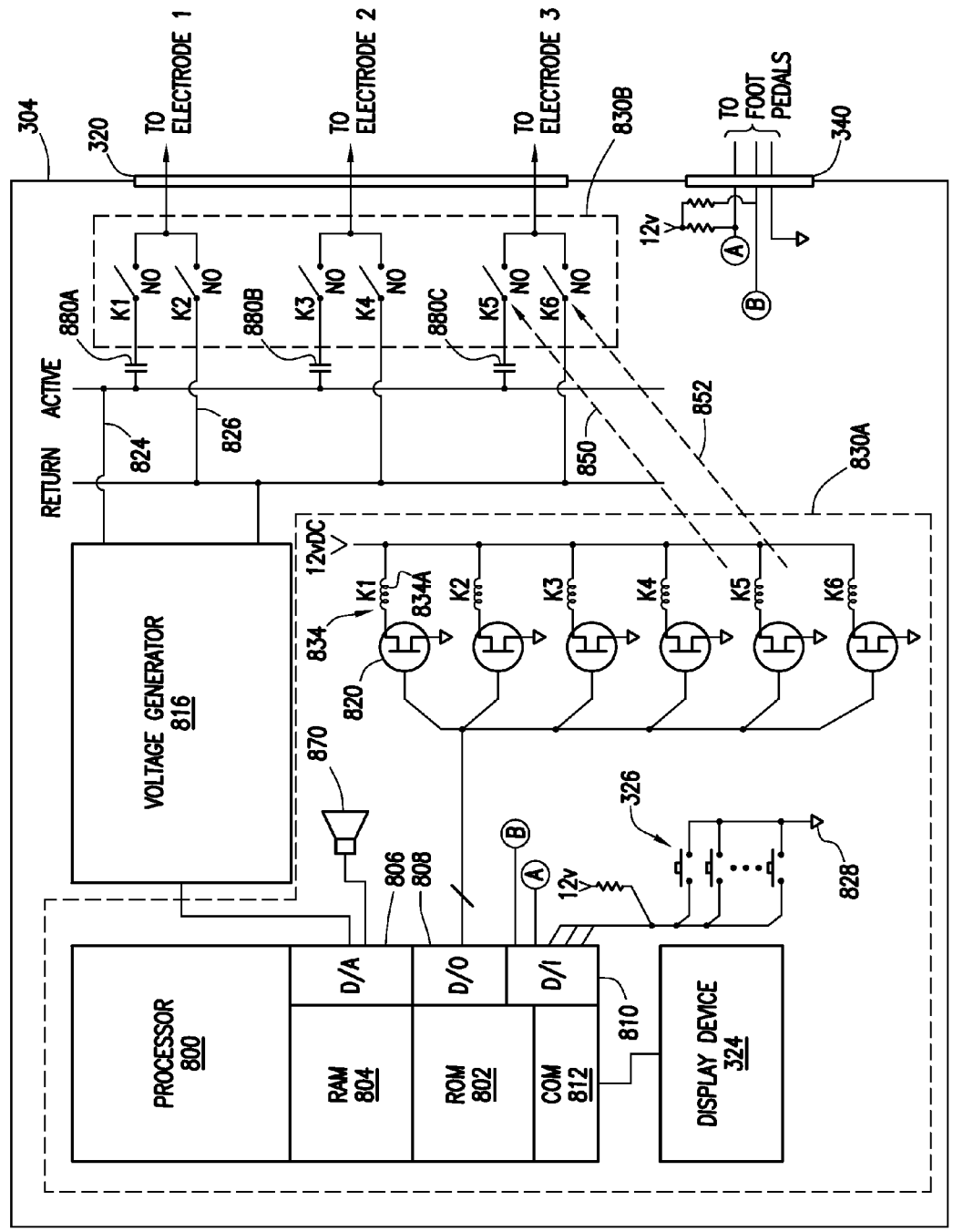
FIG. 8 shows an electrical block diagram of an electrosurgical controller in accordance with at least some embodiments.

FIG. 8 illustrates a controller 304 in accordance with at least some embodiments. In particular, the controller 304 in accordance with at least some embodiments comprises a processor 800. The processor 800 may be a microcontroller, and therefore the microcontroller may be integral with read-only memory (ROM) 802, random access memory (RAM) 804, digital-to-analog converter (D/A) 806, digital outputs (D/O) and digital inputs (D/I) 810. The processor 800 may further provide one or more externally available peripheral busses, such as a serial bus (e.g., $I^2C$), parallel bus, or other bus and corresponding communication mode. The processor 800 may further be integral with a communication logic 812 to enable the processor 800 to communicate with external devices, as well as internal devices, such as display device 324. Although in some embodiments the controller 304 may implement a microcontroller, in yet other embodiments the processor 800 may be implemented as a standalone central processing unit in combination with individual RAM, ROM, communication, D/A, D/O and D/I devices, as well as communication port hardware for communication to peripheral components.

ROM 802 stores instructions executable by the processor 800. In particular, the ROM 802 may comprise a software program that implements various operation modes, as well as interfacing with the user by way of the display device 324, the foot pedal assembly 330 (FIG. 1), and/or a speaker assembly 870. The RAM 804 may be the working memory for the processor 800, where data may be temporarily stored and from which instructions may be executed. Processor 800 couples to other devices within the controller 304 by way of the D/A converter 806 (e.g., the voltage generator 816), digital outputs 808 (e.g., electrically controlled switches 820), digital inputs 810 (e.g., push button switches 326, and the foot pedal assembly 330 (FIG. 1)), communication device 812 (e.g., display device 324), and other peripheral devices. The other peripheral devices may comprise electrode relays and/ or switches, devices to set desired voltage generator 816 output voltage, and other secondary devices internal to the generator.

Voltage generator 816 generates selectable alternating current (AC) voltages that are applied to the electrodes of the wand 302. In some embodiments, the voltage generator defines an active terminal 824 and a return terminal 826. The active terminal 824 is the terminal upon which the voltages and electrical currents are induced by the voltage generator 816, and the return terminal 826 provides a return path for electrical currents. In some embodiments, the return terminal 826 may provide a common or ground being the same as the common or ground within the balance of the controller 304 (e.g., the common 828 used on push-buttons 826), but in other embodiments the voltage generator 816 may be electrically "floated" from the balance of the supply power in the controller 304, and thus the return terminal 826, when measured with respect to the common (e.g., common 828) within the controller 304, may show a voltage difference; however, an electrically floated voltage generator 816 and thus the potential for voltage readings on the return terminal 816 does not negate the return terminal status of the terminal 826 relative to the active terminal 824.

The voltage generated and applied between the active terminal 824 and return terminal 826 by the voltage generator 616 is a RF signal that, in some embodiments, has a frequency of between about 5 kilo-Hertz (kHz) and 20 Mega-Hertz (MHz), in some cases being between about 30 kHz and 2.5 MHz, preferably being between about 50 kHz and 500 kHz, often less than 350 kHz, and often between about 100 kHz and 200 kHz. In some applications, a frequency of about 100 kHz is useful because target tissue impedance is much greater at 100 kHz. In other applications, such as procedures in or around the heart or head and neck, higher frequencies may be desirable (e.g., 400-600 kHz).

The RMS (root mean square) voltage generated by the voltage generator 816 may be in the range from about 5 Volts (V) to 1000 V, preferably being in the range from about 10 V to 500 V, often between about 10 V to 400 V depending on the active electrode size, the operating frequency and the operation mode of the particular procedure or desired effect on the tissue (i.e., contraction, coagulation, cutting or ablation). The peak-to-peak voltage generated by the voltage generator 816 for ablation or cutting in some embodiments is a square wave form in the range of 10 V to 2000 V and in some cases in the range of 100 V to 1800 V and in other cases in the range of about 28 V to 1200 V, often in the range of about 100 V to 320V peak-to-peak (again, depending on the electrode size, number of electrodes the operating frequency and the operation mode). Lower peak-to-peak voltage is used for tissue coagulation, thermal heating of tissue, or collagen contraction and may be in the range from 50 V to 1500V, preferably 100 V to 1000 V and more preferably 60 V to 130 V peak-to-peak (again, these values are computed using a square wave form).

The voltage and current generated by the voltage generator 816 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of the square wave voltage produced by the voltage generator 816 is on the order of about 50% for some embodiments as compared with pulsed lasers which may have a duty cycle of about 0.0001%. Although square waves are generated and provided in some embodiments, the various embodiments may be equivalently implemented with many applied voltage waveforms (e.g., sinusoidal, triangular).

Still referring to the voltage generator 816, the voltage generator 816 delivers average power levels ranging from several milliwatts to hundreds of watts per electrode, depending on the voltage applied to the target electrode for the target tissue being treated, and/or the maximum allowed temperature selected for the wand 102. The voltage generator 816 is configured to enable a user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the voltage generator 816 may have a filter that filters leakage voltages at frequencies below 100 kHz, particularly voltages around 60 kHz. Alternatively, a voltage generator 816 configured for higher operating frequencies (e.g., 300 kHz to 600 kHz) may be used in certain procedures in which stray low frequency currents may be problematic. A description of one suitable voltage generator 616 can be found in commonly assigned U.S. Pat. Nos. 6,142,992 and 6,235,020, the complete disclosure of both patents are incorporated herein by reference for all purposes.

In accordance with at least some embodiments, the voltage generated 816 is configured to limit or interrupt current flow when low resistivity material (e.g., blood, saline or electrically conductive gel) causes a lower impedance path between the return electrode(s) and the active electrode(s). Further still, in some embodiments the voltage generator 816 is configured by the user to be a constant current source (i.e., the output voltage changes as function of the impedance encountered at the wand 302).

In some embodiments, the various operational modes of the voltage generator 816 may be controlled by way of digital-to-analog converter 806. That is, for example, the processor 800 may control the output voltage by providing a variable voltage to the voltage generator 816, where the voltage provided is proportional to the voltage generated by the voltage generator 816. In other embodiments, the processor 800 may communicate with the voltage generator by way of one or more digital output signals from the digital output 808 device, or by way of packet based communications using the communication 812 device (the alternative embodiments not specifically shown so as not to unduly complicate FIG. 8).

In addition to controlling the output of the voltage generator 816, in accordance with at least some embodiments the controller 304 is also configured to selectively electrically couple the active terminal 824 singly or in combination to the electrodes of the wand (by way of the electrical pins of the controller connector 320). Likewise, in the various embodiments, the controller 304 is also configured to selectively electrically couple the return terminal 826 singly or in combination to the electrodes of the wand (again by way of the electrical pins of the controller connector 320). In order to perform the selective coupling, the controller 304 implements a control circuit 830, shown in dashed lines in FIG. 8. For convenience of the figure the control circuit has two parts, 830A and 830B, but the two parts nevertheless comprise the control circuit 830. In particular, the control circuit 830 comprises the processor 800, voltage controlled switches 820 and mechanic relays K1-K6. The coils of relays K1-K6 are shown within portion 830A, while the contacts for each mechanical relay are shown within portion 830B. The correlation between the coils for mechanical relays K5 and K6 and the contacts for mechanical relays K5 and K6 are shown by dashed arrow-headed lines 850 and 852 respectively. The correlation between the remaining coils and contacts is not specifically shown with arrow-headed lines so as not to unduly complicate the figure; however, the correlation is noted by way of corresponding references.

In accordance with at least some embodiments, at least three electrodes of the wand 302 are separately electrically coupled to the controller 304. Thus, the description of FIG. 8 is based on three separately electrically coupled electrodes, but it will be understood that three or more separately electrically coupled electrodes may be used. The electrical pin of the controller connector 320 for each electrode is configured to be selectively coupled to either the active terminal 824 or the return terminal 826. For example, the electrical lead configured to couple illustrative electrode 1 of FIG. 8 couples to the normally open (NO) contact terminals for the mechanical relays K1 and K2. The other side of the normally open contact for mechanical relay K1 couples to the active terminal 824 by way of capacitor 880A, while the other side of the normally open contact for the mechanical relay K2 couples to the return terminal 626. Thus, by selectively activating mechanical relay K1 or mechanical relay K2, electrode 1 can be either an active or return electrode in the surgical procedure. Alternatively, both relays can remain inactivated, and thus electrode 1 may remain unconnected.

Similarly, the electrical lead configured to couple illustrative electrode 2 couples to the normally open contact terminals for the mechanical relays K3 and K4. The other side of the normally open contact for mechanical relay K3 couples to the active terminal 824 by way of capacitor 880B, while the other side of the normally open contact for the mechanical relay K4 couples to the return terminal 826. Thus, by selectively activating mechanical relay K3 or mechanical relay K4, electrode 2 can be either an active or return electrode in the surgical procedure. Alternatively, both relays K3 and K4 can remain inactivated, and thus electrode 2 may remain unconnected. Finally with respect to the illustrative electrode 3, the electrical lead configured to couple to illustrative electrode 3 couples to the normally open contact terminals for the mechanical relays K5 and K6. The other side of the normally open contact for mechanical relay K5 couples to the active terminal 824 by way of capacitor 880C, while the opposite side of the normally open contact for the mechanical relay K6 couples to the return terminal 826. Thus, by selectively activating mechanical relay K5 or mechanical relay K6, electrode 3 can be either an active or return electrode in the surgical procedure. Alternatively, both relays can remain inactivated, and thus electrode 3 may remain unconnected.

In accordance with at least some embodiments, mechanical relays K1-K6 are selectively activated (by way of their respective coils 834) by voltage controlled switches 820. For example, when the control circuit 830 desires to couple the active terminal to electrode 1, the voltage controlled switch 820A is activated, which allows current to flow through the coil 834A of mechanical relay K1. Current flow through the coil 834 activates the relay, thus closing (making conductive) the normally open contacts. Similarly, the control circuit 830 may selectively activate any of the voltage controlled switches 820, which in turn activate respective mechanical relays K1-K6. In accordance with at least some embodiments, each mechanical relay is a part number JW1FSN-DC 12V relay available from Panasonic Corporation of Secaucus, N.J.; however, other relays may be equivalently used. Moreover, while FIG. 8 illustrates the use of field effect transistors as the voltage controlled switches 820 to control the current flow through coils of the mechanical relays, other devices (e.g., transistors, or if coils use AC driving current, triacs) may be equivalently used. Further still, in embodiments where the digital outputs 808 have sufficient current carrying capability, the voltage controlled switches may be omitted.

FIG. 8 also illustrates that the capacitors for each electrode may reside within the controller 304. In particular, capacitors 880 are representative of capacitors coupled one each in series with each electrode. It is noted that if the capacitors reside within the controller as shown in FIG. 8, the capacitors in the multi-conductor cable 312 and/or the capacitors in wand 302 may be omitted. While FIG. 8 shows the capacitors as residing between the active electrode 824 and the respective relay contacts, in other embodiments the capacitors may reside between the relay contacts and the connector 320.

Figure 9:
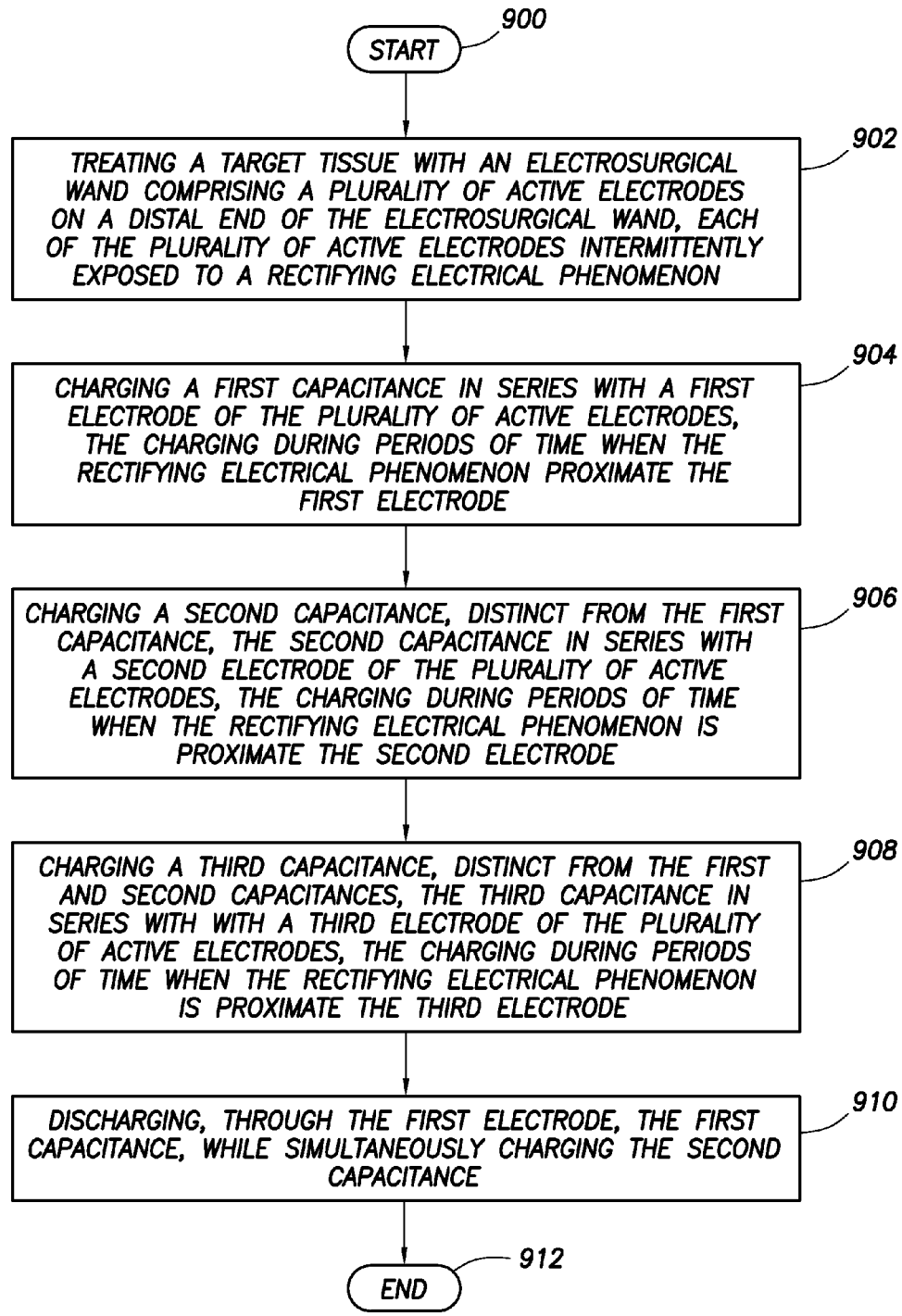
FIG. 9 shows a method in accordance with at least some embodiments.

FIG. 9 illustrates a method in accordance with at least some embodiments. In particular, the method starts (block 900) and proceeds to treating a target tissue with an electrosurgical wand comprising a plurality of active electrodes on a distal end of the electrosurgical wand, each of the plurality of active electrodes intermittently exposed to a rectifying electrical phenomenon (block 902). The method further comprises charging a first capacitance in series with a first electrode of the plurality of active electrodes (the charging during periods of time when the rectifying electrical phenomenon proximate the first electrode) (block 904), charging a second capacitance in series with a second electrode of the plurality of active electrodes (the charging during periods of time when the rectifying electrical phenomenon is proximate the second electrode) (block 906), and charging a third capacitance in series with a third electrode of the plurality of active electrodes (the charging during periods of time when the rectifying electrical phenomenon is proximate the third electrode) (block 908). And then, the method comprises discharging, through the first electrode, the first capacitance while simultaneously charging the second capacitance (block 910), and the illustrative method ends (block 912).

In vivo experiments prove that the change in capacitor configuration from a single lumped capacitance (as in FIG. 1A) to a set of discrete capacitances associated one each with each electrode (as in FIG. 1B) results in a noticeable reduction in low frequency stimulation in the animal analogue (e.g., chicken) as the number of discrete capacitances increases. For example, the most significant effect was observed when the single 50 nano-Farard (nF) capacitance was replaced with 23 discrete 2.2 nF capacitors. Experiments with three discrete capacitors (on 10 nF and two 20 nF) shows improvement over the single 50 nF capacitor set-up, but with the results less pronounced than the 23 discrete 2.2 nF capacitor set up.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. A method of reducing muscle stimulation during electrosurgical procedures comprising:
    treating a target tissue with an electrosurgical wand comprising a plurality of active electrodes on a distal end of the electrosurgical wand, each of the plurality of active electrodes intermittently exposed to a rectifying electrical phenomenon;
    charging a first capacitance in series with a first electrode of the plurality of active electrodes, the charging during periods of time when the rectifying electrical phenomenon is proximate the first electrode;
    charging a second capacitance, distinct from the first capacitance, the second capacitance in series with a second electrode of the plurality of active electrodes, the charging during periods of time when the rectifying electrical phenomenon is proximate the second electrode;
    charging a third capacitance, distinct from the first and second capacitances, the third capacitance in series with a third electrode of the plurality of active electrodes, the charging during periods of time when the rectifying electrical phenomenon is proximate the third electrode; and then
    discharging, through the first electrode, the first capacitance, during the step of charging the second capacitance.

2. The method of claim 1, further comprising then discharging, through the second electrode, the second capacitance, during the step of charging the third capacitance.

3. The method of claim 2, further comprising then discharging, through the third electrode, the third capacitance, during the step of charging the first capacitance.

4. The method of claim 1 wherein the charging of the first capacitance further comprises charging the first capacitance disposed within an enclosure that encloses a voltage generator electrically coupled to the plurality of active electrodes.

5. The method of claim 1 wherein the charging of the first, second and third capacitances further comprises charging the first, second and third capacitances disposed within an enclosure that encloses a voltage generator electrically coupled to the plurality of active electrodes.

6. The method of claim 1 wherein the charging of the first capacitance further comprises charging the first capacitance disposed within at least one selected from the group consisting of: a handle of the wand; and an elongate shaft of the wand.

7. The method of claim 1 wherein the charging of the first, second and third capacitances further comprises charging the first, second and third capacitances each disposed within at least one selected from the group consisting of: a handle of the wand; and an elongate shaft of the wand.

8. The method of claim 1 wherein the charging of the first capacitance further comprises charging the first capacitance disposed within an multi-conductor cable, the multi-conductor cable couples the plurality of active electrodes of the wand to a voltage generator.

* * * * *